(12) United States Patent
Borgos (10) Patent No.: US 9,180,172 B2
(45) Date of Patent: Nov. 10, 2015

(54) TREATMENT OF PEYRONIES DISEASE

(75) Inventor: Natalie Ann Borgos, Minnetonka, MN (US)

(73) Assignee: AMS RESEARCH CORPORATION, Minnetonka, MN (US)

( * ) Notice: Subject to any disclaimer, the term of this patent is extended or adjusted under 35 U.S.C. 154(b) by 0 days.

(21) Appl. No.: 13/327,450

(22) Filed: Dec. 15, 2011

(65) Prior Publication Data

US 2012/0156178 A1 Jun. 21, 2012

Related U.S. Application Data

(60) Provisional application No. 61/423,249, filed on Dec. 15, 2010.

(51) Int. Cl.
- *C12N 9/00* (2006.01)
- *A61K 38/48* (2006.01)
- *A61K 35/28* (2015.01)

(52) U.S. Cl.
CPC ............. *A61K 38/4886* (2013.01); *A61K 35/28* (2013.01)

(58) Field of Classification Search
None
See application file for complete search history.

(56) References Cited

U.S. PATENT DOCUMENTS

| | | | |
|---|---|---|---|
| 3,767,085 A * | 10/1973 | Cannon et al. | 222/82 |
| 6,022,539 A * | 2/2000 | Wegman | 424/94.67 |
| 6,541,039 B1 | 4/2003 | Lesniak et al. | |
| 6,866,842 B1 | 3/2005 | Chancellor et al. | |
| 6,972,005 B2 * | 12/2005 | Boehm et al. | 604/191 |
| 6,979,466 B2 | 12/2005 | Lesniak et al. | |
| 7,115,417 B1 | 10/2006 | Chancellor | |
| 7,553,662 B2 | 6/2009 | El Haj et al. | |
| 7,625,562 B2 | 12/2009 | El Haj et al. | |
| 2003/0161816 A1 | 8/2003 | Fraser et al. | |
| 2004/0013652 A1 | 1/2004 | Marko et al. | |
| 2005/0025755 A1 | 2/2005 | Hedrick et al. | |
| 2006/0039896 A1 | 2/2006 | Kleinsek et al. | |
| 2006/0045872 A1 | 3/2006 | Miguel et al. | |

(Continued)

FOREIGN PATENT DOCUMENTS

| | | | |
|---|---|---|---|
| WO | WO04/000369 | 12/2003 | |
| WO | WO 2009/120879 | * 10/2009 | C12N 5/08 |

OTHER PUBLICATIONS

Zucchi et al., JAS, 17:23-29 (2010).*
Levine et al., IJIR, 14: 324-328 (2002).*
Jordan, J. Sex. Med., 5:180-187 (2008).*
Bodner, Int. Surg., 63(6), 69-71, abstract only (1978).*

(Continued)

*Primary Examiner* — Robert Mondesi
*Assistant Examiner* — Thomas J Visone
(74) *Attorney, Agent, or Firm* — Kagan Binder, PLLC (57) ABSTRACT

The invention relates to systems and therapeutic methods to reduce plaque causing Peyronie's disease. One approach uses high pressure injection of collagenase-containing composition into a penile plaque. Plaque disruption is enhanced by the mechanical force of the high pressure, followed by the enzymatic action of collagenase. Another approach uses collagenase as a pretreatment, followed by addition of adipose-derived stem cells ADSCs. The initial collagenase injection breaks down collagen (often more type III than type I in Peyronie's) to provide short term benefit. The longer-term benefit is provided by introduction of ADSCs to the plaque, which can produce cytokines and other signals for revascularization and restoration of normal penile tissue. The resulting combination advantageously reduces the bulk of the plaque early on with ongoing reduction through the revascularization of the tissue. In addition, the treatment provides an advantageous shift of elastin and collagen ratios.

22 Claims, 6 Drawing Sheets

(56) References Cited

U.S. PATENT DOCUMENTS

| | | | |
|---|---|---|---|
| 2006/0100590 A1* | 5/2006 | Thorne et al. | 604/218 |
| 2007/0036768 A1* | 2/2007 | Fraser et al. | 424/93.7 |
| 2007/0083155 A1* | 4/2007 | Muller | 604/91 |
| 2007/0224173 A1* | 9/2007 | Koullick et al. | 424/93.7 |
| 2008/0014181 A1* | 1/2008 | Ariff et al. | 424/93.7 |
| 2008/0267927 A1 | 10/2008 | Lutz et al. | |
| 2008/0286361 A1 | 11/2008 | Dobson et al. | |
| 2008/0319417 A1* | 12/2008 | Quijano et al. | 604/522 |
| 2009/0018496 A1* | 1/2009 | Harper et al. | 604/89 |
| 2009/0082611 A1 | 3/2009 | Levy et al. | |
| 2009/0123366 A1 | 5/2009 | Dobson et al. | |
| 2009/0180965 A1 | 7/2009 | Freyman et al. | |
| 2009/0304654 A1* | 12/2009 | Lue et al. | 424/93.21 |
| 2010/0298816 A1 | 11/2010 | Dobson | |
| 2011/0034753 A1 | 2/2011 | Dobson et al. | |

OTHER PUBLICATIONS

Lin et al., J. Sex Med., 6(Suppl 3):320-327 (2009).*
Anthony Atala, M.D., Future Perspectives in Reconstructive Surgery Using Tissue Engineering, Urologic Clinics of North America, Reconstructive Urology, vol. 26, No. 1 (Feb. 1999) pp. 157-165.
Alfred E. Bent et al., Treatment of Intrinsic Sphincter Deficiency Using Autologous Ear Chrondrocytes as a Bulking Agent, Neurourology and Urodynamics 20:157-165 (2001).
Stanislav Berjukow, et al., Membrane Properties of Single Muscle Cells of the Rhabdosphincter of the Male Urethra, The Prostate 58:238-274 (2004).
Teruhiko Yokoyama et al., Persistence and Survivial of Autologous Muscle Derived Cells Versus Bovine Collagen as Potential Treatment of Stress Urinary Incontinence, the Journal of Urology, vol. 165; 171-276, Jan. 2001.

* cited by examiner

TREATMENT OF PEYRONIES DISEASE

PRIORITY

This application claims the benefit of U.S. Provisional Patent Application Ser. No. 61/423,249, filed Dec. 15, 2010, entitled TREATMENT OF PEYRONIE'S DISEASE, the disclosure of which is incorporated herein by reference.

FIELD OF THE INVENTION

The invention relates generally to surgical tools and methods and, more particularly, to methods and devices for treating Peyronie's disease.

BACKGROUND OF THE INVENTION

Peyronie's disease is characterized by the presence of dense fibrous tissue within the tunica albuginea about the corpus cavernosum of the penis, and is often associated with penile pain, curvature, or a palpable plaque. Infectious, traumatic, autoimmune and genetic causes have been proposed to be causative for Peyronie's. These characteristics are often associated with erectile dysfunction and may cause pain to the partner as well. Treating this disease has been done using injections of various kinds as well as surgical intervention to straighten the penis. More recent therapies include injecting collagenase to reduce the fibrotic tissue. The plaques have been theorized to be caused by an injury creating a break within the tunica; others have postulated that they are caused by a fibrotic disorder or unknown causes not related to injury. It is desired to provide a treatment that addresses the affected penile tissue and to address the potential for future reoccurrence of the condition.

SUMMARY OF THE INVENTION

The invention relates to methods, compositions, and systems (e.g., kits) for the treatment of Peyronie's disease. Embodiments of the invention can reduce the plaque causing Peyronie's disease in both the short and long term time frame.

One embodiment of the invention provides a combination therapy to reduce the plaque causing Peyronie's disease. The combination method comprises a step of delivering a composition comprising collagenase to a plaque in penile tissue, and then a step of delivering a composition comprising adipose-derived stem cells to the plaque, or an area of the penile tissue where the plaque existed during the step of delivering the collagenase composition. The initial collagenase administration injection breaks down the collagen plaque to provide short term benefit. The longer-term benefit is provided by the introduction of the adipose-derived stem cells to the target tissue to produce cytokines and other signals to revascularize the tissue. The resulting combination of injected material advantageously reduces the bulk of the plaque early on with ongoing reduction through the revascularization of the tissue providing longer-term benefit to the patient. The revascularization can help in clearing the tissue of the plaque breakdown products and promote re-formation of normal tissue. In addition, the treatment provides an advantageous shift of elastin and collagen ratios. The combination treatment can restore elasticity to the penis and normal function.

In another embodiment, the invention provides a therapy to reduce the plaque causing Peyronie's disease using a composition comprising collagenase which is administered using high pressure. The method comprises a step of delivering a composition comprising collagenase to a plaque in penile tissue, wherein the composition is delivered at a pressure of at least 100 psi. The force of the composition comprising collagen as generated from the high pressure delivery weakens the tissue thereby enhancing disruption of the fibrotic plaque. The high pressure delivery and can also result in a better dispersion of the collagenase throughout the plaque. Optionally, in this embodiment, the step of high pressure injection of the collagenase-containing composition can be followed by of step of delivering a composition comprising adipose-derived stem cells to the plaque, or an are of the penile tissue where the plaque previously existed. Use of high pressure, in addition to the collagenase, more aggressively breaks down the plaque tissue and can reduce the number of collagenase injections into penile tissue, resulting in a more desirable treatment regimen for a patient with Peyronie's.

Other embodiments comprise compositions and systems for the treatments of Peyronie's disease. In one embodiment, the system comprises a composition comprising collagenase, a device for enriching adipose-derived stem cells from an adipose tissue preparation, and an injection device for delivering at least the collagenase-containing composition to a penile plaque. The same injection device may also be used for delivering a composition comprising adipose-derived stem cells to the plaque. The injection device can be one that generates high pressure, such as greater than 100 psi, for delivery of the collagenase-containing composition. The device that enriches adipose-derived stem cells can optionally be configured to mix the stem cells with a matrix material, and can also optionally be configured to be connected to the injection device.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
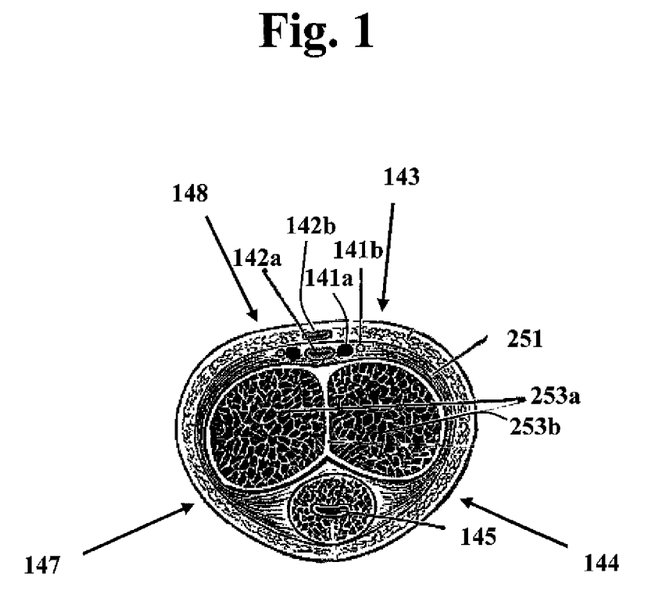
FIG. 1 is a schematic illustration of a cross section of a penis with its anatomical features.

With reference to FIG. 1, Peyronie's disease is a disorder characterized by fibrotic plaques of the tunica albuginea 251 (Bucks facia, the fibrous envelope) about the corpus cavernosum 253a and 253b, of the penis. The plaques cause penis deformation observed as curvature in many patients. Peyronie's can be considered a localized connective tissue disorder of where fibrous scar tissue replaces the normally elastic fibers and is noticed as a palpable hardening of a normally soft tissue (induration), commonly situated in the dorsum of the penis. The fibrotic plaque restricts expansion of the affected portion of the penis during tumescence. In turn, this limits the extensibility of the affected segment of the penile shaft, and causes an angled erection. Patients often can detect the presence of the palpable plaque, and can also experience painful erections. Sexual dysfunction is apparent in 30% of patients, and the main cause of impotence and loss of erection appears to be a result of veno-occlusive dysfunction. Peyronie's disease can be found in men over a wide age range (e.g., around 30 to more than 70).

Embodiments of the invention include those directed to compositions, systems, kits, and methods for the treatment of Peyronie's disease. In some embodiments, methods for the treatment of the disease include the injection of a composition containing collagenase (e.g., a "first composition" or a "collagenase-containing composition") into penile tissue, followed by the injection of a composition containing cells (e.g., a "second composition" or a "cell-containing composition") into penile tissue. In some embodiments, methods for the treatment of the disease include the high pressure injection of a composition containing collagenase into penile tissue. In some modes of practice, the invention includes first injecting the target penile tissue with collagenase. Then a cellular mixture is introduced to promote re-vascularization of the target tissue.

The method and system used to deliver the collagenase can include one or more injection devices for delivering the collagenase-containing composition and cell-containing composition to a plaque in the penile tissue, or an area of penile tissue where the plaque existed. The injection device for delivering the composition to collagenase-containing composition can have features allowing for high pressure delivery of the composition. The cell-containing composition can be injected into the plaque using the same device as used to inject the collagenase-containing composition, or a different injection device can be used. The system of the invention includes a collagenase-containing composition, an injection device, and optionally one or more components for the removal of adipose tissue, the enrichment of adipose derived stem cells, and/or the mixing of adipose stem cells with a cellular matrix component. Other system components which can optionally be incorporated in optional steps of the invention include anesthetics and antibiotics; surgical instruments such as scalpels, forceps, needles, and sutures; and bandages and tapes. The optional components can be used to numb, prevent infection, and/or repair tissue in the patient. Tissue sites affected by treatment or surgical intervention include penile tissue and a tissue site from which adipose tissue can be removed from the patient, such as the abdomen.

Collagenase is a hydrolytic enzyme that acts as an endopeptidase to digest collagen in its helical region. Collagenases can be obtained from bacterial and vertebrate sources. Bacterial collagenase, such as obtained from *Clostridium hystolyticum*, can degrade almost all collagen types exhibits and can degrade both water-soluble denatured and water-insoluble native. Collagenase is a $Zn^{2+}$-containing metalloenzyme that requires $Ca^{2+}$ for binding to collagen substrates. Commercially available preparations of *Clostridium histolyticum*, collagenases are available in several levels of purity, such as from Worthington Biochemical Corp. (Lakewood, N.J.). Metals other than $Zn^{2+}$ and $Ca^{2+}$ inhibit collagenase activity, as well as compounds such as EDTA, which binds $Ca^{2+}$ inhibit enzyme activity.

The collagenase-containing composition can include collagenase in an amount or concentration sufficient to provide desired enzymatic activity following injection into a treatment site in penile tissue. For example, the composition, following injection into penile tissue, can have an amount of collagenase sufficient to cause the softening and/or rupture the plaque. In some preparations collagen is present at a concentration in the range of about $2 \times 10^4$ to about $4 \times 10^4$ ABC units per mL, with one unit of collagenase being defined capable of solubilizing ninhydrin reactive material equivalent to 1.09 nanomoles of leucine per minute, based on the digestion of undenatured collagen (from bovine tendon) at pH 7.2 and 37° C. for 20-24 hours.

The collagenase can be present in a pharmaceutically acceptable liquid carrier. Exemplary aqueous liquid carriers can include one or more or physiologically acceptable salts and or buffers, such as sodium chloride and calcium chloride; other excipients or stabilizers can be present, such as dextran.

In some preparations, $Ca^{2+}$ can be present in the composition in an amount to promote collagenase activity. $Zn^{2+}$ can be also present in the composition. A preferred pH for the collagenase composition in the range of about 6 to about 8. The collagenase can be supplied as part of system (e.g., a kit), which can be used in accordance with methods of the invention. The collagenase can be in dry form (e.g., lyophilized) and can be reconstituted into a liquid composition with a suitable aqueous solution, which can also be supplied with the system, or can be provided with the system solubilized form.

As used herein, "collagenase treatment regimen" refers aspects associated with the injection of the collagenase-containing composition, including dose (amount), course of treatment, and location of injection(s). Injection of the collagenase-containing composition into the penile tissue can be carried out in accordance with a desired treatment. The size, severity, and number of plaques present in the penile tissue can be determined prior to collagenase injection, in order to plan a desired injection regimen. Injection volume(s) and injection locations can be predetermined based on a physical assessment of penile tissue.

Many plaques found in Peyronie's disease are located near the base of the penis, such as those plaques thought to arise due to non-traumatic injury, e.g., auto-immune disease. However, plaques believed to arise due to traumatic injury of the penile tissue are more often located midshaft. With reference to FIG. 1, the collagenase-containing composition is typically injected into one or more locations on the dorsal half of the penis, and avoid the dorsal arteries 141a and 141b veins 142a and 142b. Injection locations are commonly between 1 and 4 o'clock (between arrows 143 and 144) and between 8 and 11 o'clock (arrows 147 and 148) respectively. The urethra is shown with reference to 145.

In exemplary modes of practice, the volume of a single injection of collagen composition into a fibrous plaque is in the range of about 0.1 mL to about 1 mL, or about 0.25 mL to about 0.75 mL. A single injection volume refers to the total amount of collagen composition delivered from the distal end of an injection device with any needle configuration (e.g., single or multi-needle, having a single exit aperture or multiple exit apertures) when placed in the tissue. If the plaque is large, a series of smaller injections may be made into different portions of the plaque. Exemplary total amounts of collagenase injected into a single plaque can range from about $1\times10^4$ to about $4\times10^4$ ABC units.

In some modes of practice, collagen injection is carried out using a syringe and needle combination, with the flow of the collagenase-containing composition controlled manually (i.e., with forces from the hand) by a practitioner during administration. In this mode of practice injection pressure can be increased by applying more force on the plunger of the syringe, by using a smaller gage needle, or both. Exemplary needles for collagenase injection have a size in the range of about 18 gauge to about 27 gauge, and preferably about 20 gauge to about 25 gauge. The tip of the needle can be moved through the dermis and into the plaque, and the needle preferably penetrates to a sufficient depth in the penile tissue.

In some modes of practice, the collagenase composition is injected into a plaque using a high pressure injection. In addition to the enzymatic action of the collagenase, the high pressure of injection of the collagenase composition can enhance plaque removal by mechanically disrupting the plaque tissue though the force of the high pressure injectate. In addition, the high pressure can provide a better dispersion of the collagenase throughout the plaque. Use of an injection device that includes a pump to generate the high pressure is one technique for carrying out the collagenase injection.

Figure 2:
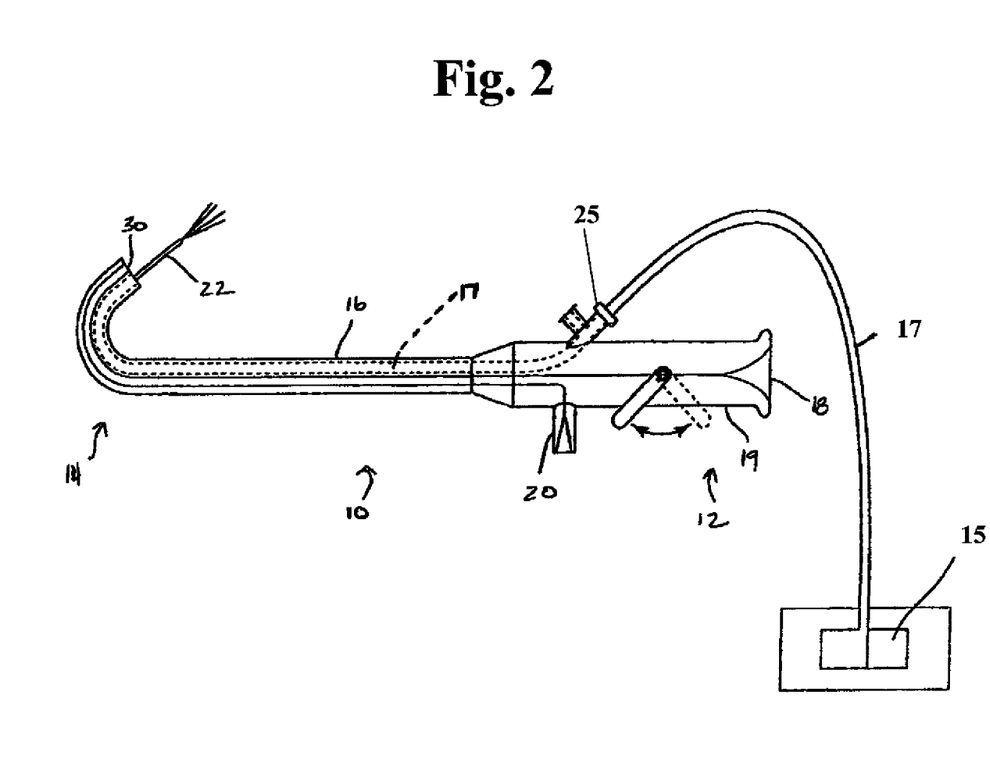
FIG. 2 is an illustration of an injection system in accordance with embodiments of the present invention.
Figure 3:
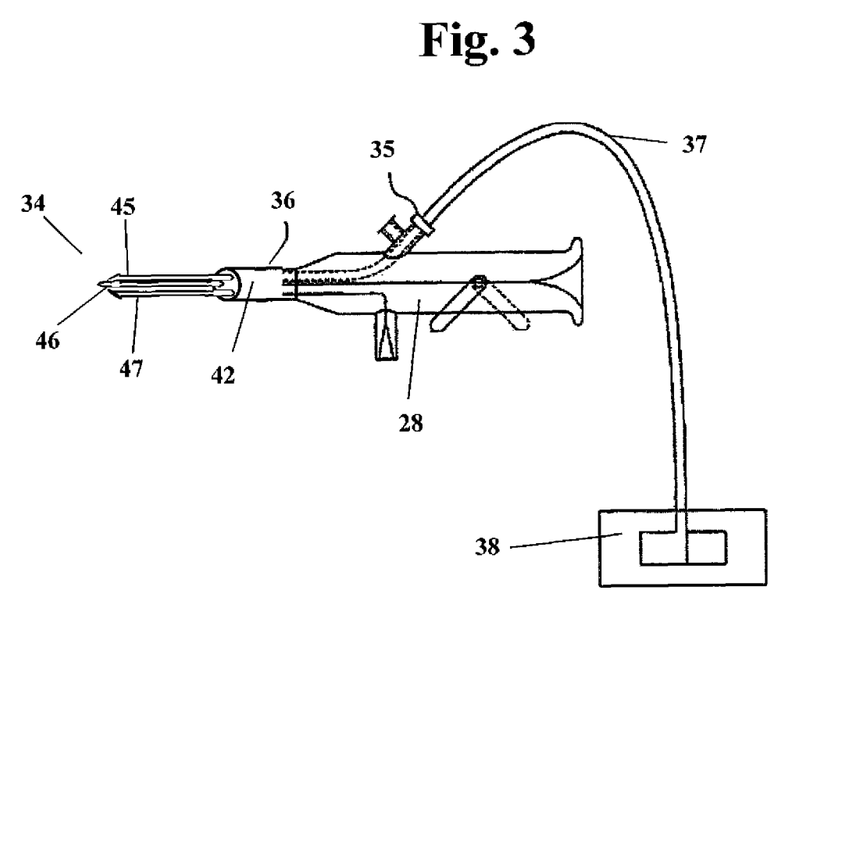
FIG. 3 is an illustration of an injection system in accordance with embodiments of the present invention.

In one embodiment, the collagenase-containing composition is introduced into the plaque using an injection tool with high pressure, such as shown in FIG. 2 or FIG. 3. In some arrangements, the injection device can include multiple ports or multiple needles to push the collagenase out at a fast rate into the middle of the plaque. In addition to the enzymatic action of the collagenase, the force of the injected composition helps to more quickly break apart the plaque by weakening the tissue.

The high pressure injection device generally includes a distal end and a proximal end. The "distal end" refers to a portion of the device that has one or more needles that can pierce the penile plaque. The needles may be stationary or "fixed" on the distal end, or can be movable and extendable from within a lumen or shaft of the distal end of the device so that they pierce the plaque. The distal end may also include optional functional features that operate on tissue during use, such as a frictional tissue holding tip, or a light. The "proximal end" of an exemplary high pressure injection device can include an injector body or "console" that remains external to the patient during use. An exemplary console can include a housing that connects to or is otherwise (directly or indirectly) in fluid communication with the injection needle(s). The console can include fluid that can be pressurized by a pressure source to cause the fluid to flow to the needles for injection into the penile plaque at the distal end.

With reference to FIG. 2, the injection device or system 10 can include a proximal portion 12 and a distal portion 14, and a shaft or body portion 16 extending therebetween. The proximal portion 12 generally includes a handle 18, and a connection port or assembly adapted to interconnect with a fluid source 15. The fluid source 15 is in operative and fluid communication with the proximal portion 12 via a conduit 17. The distal end of the conduit 17 can be removably connected to an input port 25 located on the handle 18 of the device. The fluid source 36 can include a reservoir and pressure source capable of pressurizing and advancing fluid contained in the source. The fluid source can be generally "remote" from the proximal portion or the distal portion 14, or provided generally proximate or directly attached to the device components.

A working lumen or channel 17 extends within the shaft 16 and contains a fluid delivery lumen 22 such that the lumen 22 is adapted to move longitudinally along the length of the body 16 to allow the distal end of the fluid delivery lumen 22 to extend from the tip of the distal portion 14 as an orifice extension. The high-pressure injectate (collagen-containing composition) is delivered to the penile tissue from the fluid delivery lumen 22. In particular, the injectate traverses from the fluid source 15, into the working channel 17, and out of the fluid delivery lumen 22. Optionally, shaft 16 can include a fiber optic feature 30, e.g., an endoscope device, having a light source 20 to transmit light to the distal portion 14.

In another embodiment, with reference to FIG. 3, the injection device or system 30 can include a short and stiff shaft 36 between the handle 38 and distal end 34 of the device. The fluid delivery lumen 42 within the shaft 36 can be connected to one or more needles (45, 46, 47) on the distal end of the device. The distal end of the conduit 37 can be removably connected to an input port 35 located on the handle 38 of the device.

The high pressure injection device, such as one shown in FIG. 2 or 3, ejects a therapeutic "fluid" from a needle located on the distal end of a shaft into the plaque. The process of high pressure injection may be referred to as "jet injection." In some arrangements, the distal end of the device can include multiple needles, multiple apertures in a single needle, or multiple apertures among multiple needles. The multiple needles or multiple apertures can be stationary or moveable relative to a shaft of the device, for ejecting a pressurized collagenase-containing composition at multiple locations and/or in multiple directions in the plaque. Embodiments that include multiple apertures or multiple needles can include an extended, expanded, or extendable chain, string, array, or sequence (e.g., "daisy chain"). Apertures may be located at an extension mechanism ("aperture extension") such as extendable or fanning needles.

One configuration of the injection device includes multiple needles located on the distal end of the high pressure injection device. For example, the distal end can have two, three, four, five, or more needles emanating from the distal end of the device. Some or all of the needles on the distal end can be arranged parallel to each other, or not parallel to each other. The needles can be fixed in place on the distal end of the injection device, or can be movable, such as movable out of the distal end of the device and can penetrate into the plaque during injection. If the needles are in a fixed arrangement on the end of the device, they can be of a certain length or lengths useful for penetrating a desired depth into the penile plaque. The point at which the proximal end of a needle is attached to the distal end of the shaft can provide a stop point for movement during injection.

The needle or needle can also include one or more apertures (opening) that can be present on the distal (beveled) end of the needle, and/or along the length of the needle, such as in the needle wall. A needle with multiple apertures can allow better distribution of the collagenase composition throughout the plaque and can also provide better disruption of the plaque tissue.

Figure 4:
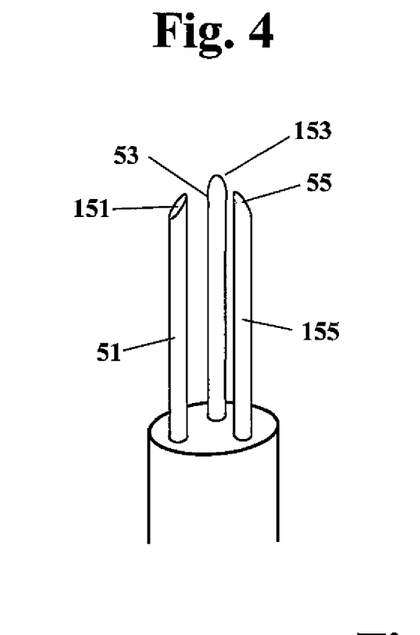
FIG. 4 is an illustration of a multi-needle distal end of an injection system in accordance with embodiments of the present invention.

FIG. 4 shows one embodiment of a distal end of a high pressure injection device having needles 51, 53, and 55, wherein the needles are parallel to each other, the needles having openings 151, 153, and 155 at the distal end of the needle, and are the same or approximately the same length. Using this configuration and in some modes of practice, when the needles are driven into the plaque, the composition can be injected into the plaque at approximately the same depth.

Figure 5:
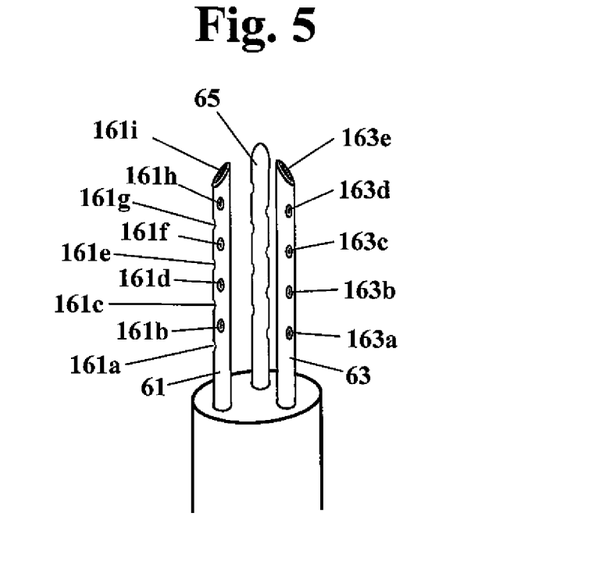
FIG. 5 is an illustration of a multi-needle distal end of an injection system in accordance with embodiments of the present invention.

FIG. 5 shows another embodiment of a distal end of a high pressure injection device having needles 61, 63, and 65, wherein the needles have multiple openings in the wall of the needle along its length. The openings can be spaced about the circumference of the needle or can be located predominantly on one side of the needle. For example, apertures 161a-161h of needle 61 face outwardly from the central axis of the distal end of the device, and direct the composition outward and in a direction generally perpendicular to the axis of the needle. The needle(s) can have one or more series of apertures (e.g., 161b, 161d, 161f, and 161h; and 163a, 163b, 163c, and 163d) aligned longitudinally on the needle. The openings can be located more towards the distal end, the proximal end, or can spaced from the distal to proximal end. The distal ends of the needles can have openings (e.g., 161i, 163e) or can be closed. A needle with multiple apertures can allow better distribution of the collagenase composition throughout the plaque and can also provide better disruption of the plaque tissue.

Figure 6:
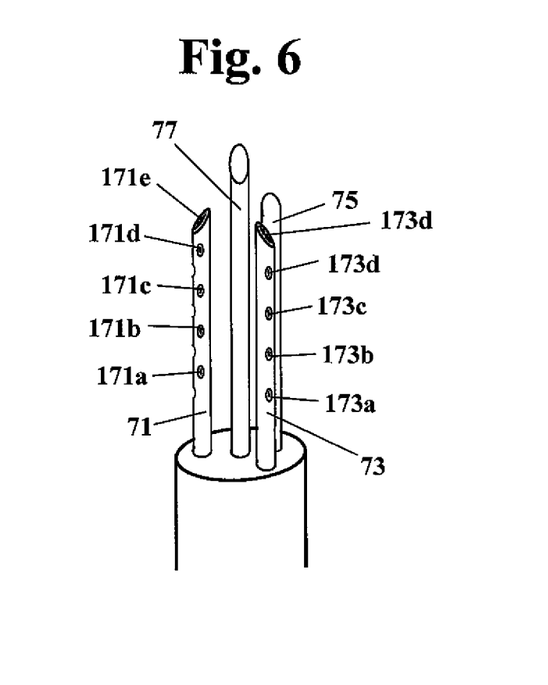
FIG. 6 is an illustration of a multi-needle distal end of an injection system in accordance with embodiments of the present invention.

In another embodiment, the distal end of the high pressure injection device has multiple needles and one or more of the needles are of different lengths. For example, FIG. 6 shows a distal end of a high pressure injection device having needles 71, 73, 75, arranged closer to the periphery of the device, and needle 77 arranged centrally and having a length that is greater than needles 71, 73, or 75. The needles 71, 73, 75, and 77 can be arranged are parallel to each other. The needles can have multiple openings in the wall of the needle along its length (e.g., 171a, 171b, 171c, and 171d; and 173a, 173b, 173c, and 173d). Using this configuration, when the needles are driven into the plaque, the composition can be injected into the plaque at different depths.

Figure 7A:
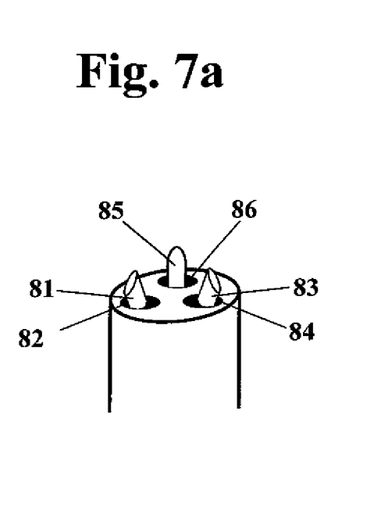
FIGS. 7a and 7b are illustrations of a multi-needle distal end of an injection system in accordance with embodiments of the present invention.
Figure 7B:
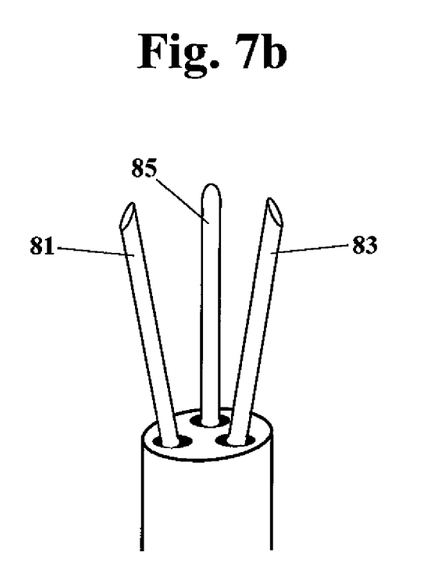

FIG. 7a shows another embodiment of a distal portion of a high pressure injection device having a lumen and ports 82, 84, and 86. Needles 81, 83, and 85 are connected to a fluid delivery conduit (not shown) within the lumen, and movable in the lumen and out of the ports from the distal end. Movement of the needles can be controlled by movement of the fluid delivery conduit so that the needles extend from the ports and pierce the plaque. In some configurations, and as shown in FIG. 7b the needles 81, 83, and 85 emerge from the ports of the distal end in a non-parallel manner so the needles spread out into the plaque when they penetrate it. In other configurations the needles can emerge from the ports in a substantially parallel manner.

In yet another embodiment, the injection device has a single needle that has multiple apertures. The single needle can have any desired aperture arrangement, such as according to any one needle in any of the multiple needle embodiments illustrated in FIGS. 4-7a.

The pressurized fluid source can include a source of fluid and a source of pressure. The pressure source can include a mechanical feature (such as a spring), a pneumatic feature, a hydraulic feature, or an electric feature, etc., to generate the fluid pressure. Further, the pressure source may be mechanically or electronically controlled. The pressure source can cause a fluid contained in a fixed or variable volume chamber to be pressurized to a transient pressure, at the injection orifice, that is sufficiently high to allow the fluid to be ejected from the injection orifice with sufficient force to penetrate the penile plaque.

A fluid stream or jet of collagenase composition ejected from an aperture of apertures of a needle into the plaque can be of a size (e.g., diameter), velocity, pressure, and volume to penetrate directly through all or a portion of the plaque, then disperse within the plaque. The stream can be considered to be a relatively high velocity, high pressure, small diameter jet that enters and disperses within the plaque. The collagenase composition can be carried as a multi-directional collection of particles (e.g., a "cloud") or droplets within the plaque. Exemplary pressures of a fluid at a pressure chamber can be at least 100 pounds per square inch (psi), for example, such as in the range of about 140 psi to about 4000 psi. Exemplary pressures for injecting penile plaques for the treatment of Peyronie's are in the range of about 140 to about 2000 psi. The injection pressure refers to the stagnation pressure of the impinging jet (average pressure within the cross section of the jet), which is an important factor that determines the penetration capability of the injected fluid.

The duration of injection of the fluid stream or jet of the collagenase-containing composition can be performed for a desired period of time. In some methods of injecting, the duration of injection is controlled by one or more feature(s) of the injection device, such as a solenoid or valve, in order to meter the flow of the composition from a needle. The injection can include one or more high pressure "pulses" of the composition from a needle. The duration of a pulse can be short such as in the range of about 5 milliseconds to about 1 second, or more specifically in the range about 50 milliseconds to about 0.6 second. Treatment can include a series of short pulses to deliver a desired amount of composition to the penile plaque, such in the range of about 0.1 mL to about 1 mL. In some modes of practice, the needle is moved within the plaque between pulses to slightly change the direction and/or location of the injected collagenase-containing composition.

Various device structures, components, methods and techniques described and depicted in U.S. Patent Publication No. 2006/0129125 and International Publication No. WO2007/079152 are envisioned for use, alone or in combination, with the present invention. As such, the entire disclosures of the above-referenced publications are incorporated herein by reference.

The collagen injections can be performed in a single treatment period, or over multiple treatment periods. For example, in one mode of practice, one or multiple collagenase injections are performed in a first time period (e.g., within an hour or less), optionally followed by injection of a cell composition (second composition). In other modes of practice, the collagenase injections are performed over multiple time periods. For example, one or more collagenase injections can be performed within a first time period, optionally followed by a cell composition injection during the first time period, following by a period where there is no treatment, such as in the range of hours to days, then followed by a second treatment period involving one or more collagenase injections, and optionally followed by a further cell composition injection during the second time period. The desired course of treatment can be determined by various factors, including the severity of the plaque formation, and the amounts of collagenase and cellular material injected into the penile tissue during the treatment regimen.

Following injection of the collagenase composition (and optionally cellular composition) the penis can be and bandaged and/or immobilized. In some modes of practice, following the collagenase treatment the penis is prevented from substantial movement for a desired period of time (for example, hours to days).

The treated penis can be monitored over the course of weeks or months to assess efficacy of the treatment. After a period of time, the penis can be reassessed for improvement as reflected by dissolution of the plaques, and straightening of the penis. If the previous treatment regimens are deemed inadequate or incomplete, a further series of treatments can be carried out using the collagenase composition.

The amount and concentration of collagenase used can be effective to soften and/or rupture the plaque. The deformity caused by the plaque that has been holding the penis bent being thus relieved, the penis soon straightens to a considerable extent, often completely. Following the collagen injection, the penis can be bandaged, such as with a compression wrap.

The same injection device used to introduce the collagenase-containing composition could be used to delivery cells to the penile plaque, or the area of the penile tissue where the penile plaque existed. For example, the injection device used to delivery the collagenase-containing composition could subsequently deliver cells into the same treatment region of the penile plaque, at a much slower fluid delivery rate to reduce sheer forces impacting the cells upon delivery. For example, referring back to FIG. 2, in some modes of practice, the conduit 34 can be removed from the input port 25, and then a cell delivery conduit (not shown) can be connected to the same input port 25. A cell composition could then be moved through the injection device or system 30 and fluid delivery lumen 22, and out of the one or more needles on the distal end of the device.

Methods of treating Peyronie's can also include delivering a composition containing cells to the penile plaque, or the area of the penile tissue where the penile plaque existed following the collagenase treatment. This cellular therapy can be performed following high pressure or low pressure injection of the collagenase-containing composition using. It is appreciated that in some modes of treatment, the collagenase composition, used optionally with high pressure delivery, can change the properties of the plaque so it is physically different as compared to the condition prior to treatment. The injected cells can promote re-vascularization and return to normally functioning penile tissue. In one mode of practice, adipose derived cells (ADCs) are removed from adipose tissue and introduced to the treatment region following the use of collagenase to break apart the connective tissue.

Adipose (i.e., fat) tissue includes or yields a high number of desirable cell types, including stem cells. Systems and methods of the invention can include devices, tools, and methods for the preparation of a composition containing a cell population derived from adipose tissue. To obtain an adipose tissue sample, a lipectomy surgical procedure can be performed. Adipose tissue obtained by lipectomy can be processed and then the cell preparation obtained can be reintroduced into the penile tissue of the same patient, thereby providing an autologous source of cells.

The adipose tissue can come from anywhere in the body. In one embodiment, the adipose tissue is obtained from the abdominal area of the patient. Other common areas may include the thigh and back area of the patient. To provide an adequate amount of cells for injection into the penile tissue for treatment of Peyronie's, adipose tissue in an amount in the range of about 60 cc to about 120 cc is obtained from the patient. If desired, a portion of the adipose tissue is set aside for preparing a "cell matrix" which can be remixed with an enriched population of cells from the adipose tissue.

In some modes of practice, adipose tissue is processed to separate the adipose-derived stem cells from the other material including other cellular and non-cellular material in the adipose tissue. Preparation methods can include steps of washing the tissue, treating the tissue with collagenase or trypsin, or optionally with mechanical agitation. Liposomes, which are generally aggregated, can be separated from free stromal cells which include the stem cells and other cells such as red blood cells endothelial cells, and fibroblast cells, by centrifugation. Erythrocytes can be lysed from the suspended pellet and the remaining cells can be filtered or centrifuged. Optionally, cells may be separated by cell sorting or separated immunohistochemically. Methods for the preparation of adipose-derived stem cells are described in commonly-assigned application number WO 20091120879.

In other modes of practice, the adipose tissue is processed to remove partially or substantially non-cellular components, and to form a heterogenous cell mixture. The heterogenous cell mixture can include endothelial cells, endothelial precursors and progenitors, mesenchymal stem cells, vascular smooth muscle cells, fibroblasts, pericytes, macrophages, and the like.

PCT Application PCT/US2010/041508 describes methods and apparatus for the preparation of cellular material useful for introduction into the penile plaques. Cell separation equipment is also commercially available from, for example, Tissue Genesis, Inc. (Honolulu, Hi.).

After a population of the adipose-derived cells (e.g., stem cells) is enriched, the cells can be introduced into or around the area of the penile plaque previously treated with a collagenase-containing composition. In other modes of practice, the adipose-derived cells are mixed with one or more materials that provide a "cell matrix" for the injected cells. The cell matrix can be chosen from synthetic components, natural components, or mixtures thereof, and can improve one or more of the following properties at the site of injection: cell viability, cell retention, cell differentiation, and cytokine production.

In some embodiments, the cell matrix can include platelet rich plasma (PRP) or platelet poor plasma (PPP). PRP is blood plasma enriched with platelets. Through degranulation of the platelets, PRP can release different cytokines that can stimulate healing of soft tissue. Processes for PRP preparation include the collection of centrifugation of whole blood which separates PRP from platelet-poor plasma and red blood cells. In some cases, the adipose-derived stem cells are combined with PRP and injected into the area of the penile plaque following injection of the collagenase-containing composition for cell based therapy. The healing proteins in PRP are advantageous and can assist in making areas of the injected tissue "sticky" for the attraction and retention of the treatment cells. PRP also includes many regenerative proteins to hasten healing. The adhesive or retention function of PRP can prevent cells from migrating or being lost through vascular flow.

In some embodiments, the cell composition with adipose-derived stem cells includes platelet poor plasma (PPP). PPP is typically characterized by a very low number or platelets (<50000/uL) and a high concentration of fibrinogen. PPP can be prepared in a centrifugation process that separates it from PRP and red blood cells. PPP can provide an autologous scaffold-like material to keep injected cells local to penile plaque to improve the regenerative potential of the cells. PPP can be beneficial to tissue as well. The PPP can include a porous gelatinous material to keep cells local to the injection site and provide a therapeutic effect. PPP can allow the movement of cytokines and other signaling molecules in and out of the tissue for regenerative mechanisms local to the injection site.

In some modes of practice, the cell matrix is prepared from a portion of the adipose tissue obtained from the patient. To prepare the cell matrix, the adipose tissue can be disaggregated by mechanical force, such as by cutting, chopping, or mincing the adipose tissue. Generally, for this cell matrix preparation, collagenase or trypsin (enzymatic) digestion is not performed to maintain the scaffolding features of the adipose tissue. The adipose particles generated using such a process are sized for penetration into the penile tissue. Grinding and filtering parameters can also be employed depending on the particular treatment site needs.

In some preparations, the cells are mixed with the disaggregated adipose tissue at a weight ratio in the range of about 1:1 to about 1:4. Methods for the preparation of an adipose tissue-derived scaffolding for cells are described in commonly assigned International Application PCT/US2009/038426 (WO2009/120879), and are described further herein with reference to the multi-chamber mixing and delivery systems.

The cell containing composition for injection into a penile plaque, or area of the penile tissue where the penile plaque existed, can be of a desired volume based on factors such as the size of the plaque, and the method and apparatus used to deliver the cell-containing composition. In exemplary modes of practice, the volume of a single injection of cell-containing composition into a fibrous plaque is in the range of about 0.1 mL to about 1 mL, or about 0.25 mL to about 0.75 mL. A single injection volume refers to the total amount of cell-containing composition delivered from the distal end of an injection device with any needle configuration (e.g., single or multi-needle, having a single exit aperture or multiple exit apertures) when placed in the tissue. If the plaque is large, a series of smaller injections may be made into different portions of the plaque.

The cell-containing composition can also include an amount of solids material that are not cells derived from the adipose tissue. For example, this solids material can include cell matrix material such as natural or synthetic polymeric material, material from PRP or PPP, or cell scaffolding derived from mechanically processed adipose tissue. In exemplary embodiments the ratio (weight) of the cellular material from the adipose tissue to the cell matrix material is in the range of about 1:1 to 1:4 or more specifically in the range of about 1:1 to about 1:2.

The cell-containing composition can optionally include biologics or drugs which can enhance the effectiveness of the cells following injection into the penile tissue, or that can further improve the condition of the tissue. Optionally, the cell-containing composition can include excipients additives or auxiliary substances such as an antioxidants, antiseptics, isotonic agents, and buffering agents.

In some modes of practice, the treatment method can include the optional additional step of delivering a "cell retaining" composition to the penile tissue that helps maintain the cells in area of injection. This composition can have a higher viscosity and act akin to a liquid bandage to keep the cells in a desired location to enhance cell therapy. The composition can be laid into the desired area of penile tissue, for example, beneath the dermis so that is contiguous with the facia. The composition can be a PRP or PPP composition, as described herein that is not required to include cells, but that optionally can include cells. In some modes of practice, a cell composition is delivered into the penile tissue, and then the cell retaining composition is delivered at a location on penile tissue that is peripheral to the location the cells were deposited.

Figure 8:
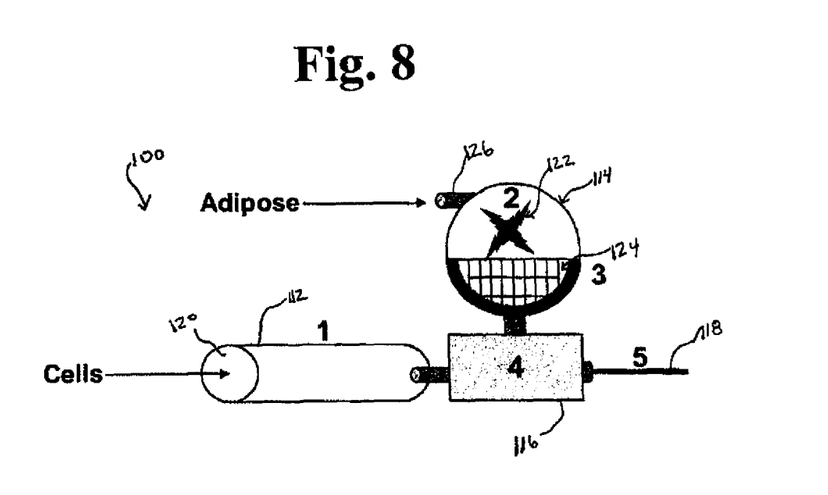
FIG. 8 is an illustration of a multi-chamber cell mixing system in accordance with embodiments of the present invention.
Figure 9:
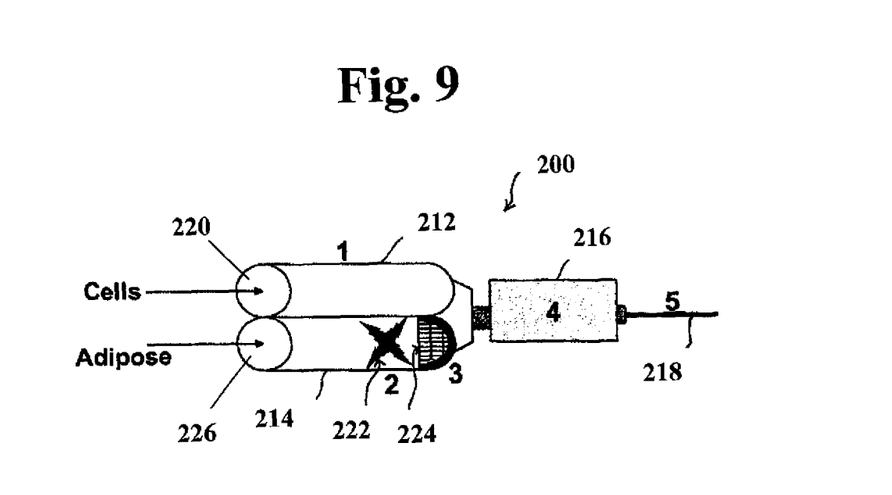
FIG. 9 is an illustration of a of a multi-chamber syringe system in accordance with embodiments of the present invention.

Referring to FIGS. 8 and 9, exemplary embodiments of a multi-chamber mixing and delivery systems 100 and 200, respectively, are shown. These devices, and the like, can be used to prepare cell-containing compositions, such as ADSC compositions, for introduction into penile tissue. The devices can also be used for the injection process.

Systems 100 and 200 can include various components and elements to facilitate mixing, digesting, filtering and injecting cellular mixtures, e.g., cells and autologous adipose tissue or scaffolding material, into penile tissue of a Peyronie's patient for treatment. The various components of the systems 100 and 200 can be constructed of materials such as polymers, metals, and other like materials compatible for use with such injection systems and methods.

Devices, methods, and compositions prepared therefrom, including those disclosed in U.S. Patent Publication Nos. 2005/0177100, 2006/0100590, 2007/0224173, 2008/0014181, 2008/0287879 and 2009/0018496; U.S. Pat. No. 7,101,354; and PCT International Patent Publication No. WO2008/091251 can be used are envisioned for use in the systems and methods of the current invention, and their disclosures are incorporated herein by reference in their entirety.

As depicted in the embodiment of FIG. 8, the system 100 can include a first syringe chamber 112, a second syringe chamber 114, a mixing element 116, and a needle 118. Optionally, the needle 118 can be replaced by a conduit which allows cells to be transferred to an injection device such as depicted in FIG. 2 or 3 so the cells can be delivered to an input port 25 or 35, respectively. Referring back to FIG. 8, the first syringe chamber 112 includes an interior portion or lumen defined therethrough and can further include an inlet port or opening 120. The second syringe chamber 114 can include a grinder or digestion element 122 (e.g., grinder, mincer or chopper device), as well as a filter or mesh element 124. The grinder element 122 can include spinning blades or members, and can be driven mechanically, manually or electrically. The filter element 124 can be a static or dynamic device. The second syringe chamber 114 can further include an inlet port or opening 126. The first syringe chamber 112 is generally adapted to receive and advance various cells, while the second syringe chamber 114 is adapted to receive and advance scaffolding tissues, such as adipose.

In another arrangement, as shown in FIG. 9, the system 200 includes a first syringe chamber 212 and a second syringe chamber 214 which are arranged side-by-side, and lead into a common conduit 228 prior to entering the mixing element 216. The system also includes a grinder or digestion element 222, a filter or mesh element 224, a cell inlet port 220, and an adipose tissue inlet port 226. Optionally, needle 218 can be replaced by a conduit which allows cells to be transferred to an injection device such as depicted in FIG. 2 or 3 so the cells can be delivered to an input port 25 or 35, respectively.

A portion of the adipose tissue that is obtained from the patient half can be washed and processed via the second chamber 114 (or 214), while the first chamber 112 (or 212) receives the heterogeneous or enriched cell (e.g., adipose derived stem cell) population that has been processed as described herein.

Prior to advancement to the mixing element 116, the adipose tissue or particles within the second syringe chamber 114 can be reduced in size at the grinder element 122, and then passed through the filter or mesh element 124. As such, adipose tissue of varying sizes and shapes can be reduced to a desirable and predefined dimension before passing through for mixing with the cells of the first syringe chamber 112 at the mixing element 116. The ideal or predefined dimensional requirements for the adipose particles can be chosen based on the desired mode of treating the penile plaque. The actual dimensional requirements can vary greatly depending on the attributes and characteristics of the plaque, or the particular course of treatment for the plaque following the collagenase-composition injection.

The mixing element 116 is in fluid and operative communication with the first syringe chamber 112, the second syringe chamber 114, and the needle 118. The mixing element 116 assists in ensuring that the cellular mixture does not separate prior to injection into the treatment site. Various known components, structures and techniques can be used to mix and retain the cellular mixture of adipose and cells received from the chambers 112, 114 into the mixing element 116 prior to injection into the target tissue through the needle 118, or for delivery to an input port 25 or 35, of a system 100 or 200, respectively. In addition, a controlled dispensing component or element can be provided at or in communication with the mixing element, or other components of the system 100, to prepare or deliver a certain or predefined number of cells, cell volume, or rate of cells to the target tissue site.

One or more plunger devices or systems can be included to facilitate advancement of the cells, adipose, and cellular mixture through the system 100 and out the injection needle 118. In addition, the needle 118, or other components of the system 100, can include a stop (not shown) or other selectively adjustable structure to ensure that the needle travels to a desired or predetermined depth within the target tissue. The stop can be sized, such as a flange, to abut against the outside of the target tissue so that only the remaining length from the stop to the distal end of the needle 118 will penetrate tissue. Further, various known attachment and sealing components, structures and techniques, e.g., Luer locks and rubber septums, can be used to interlock or connect the various components of the syringe system 10.

As depicted in the embodiment of FIG. 8, the syringe chambers 112, 114 can be disposed in a generally parallel or adjacent configuration. Again, the second syringe chamber 114 can be adapted for receiving, grinding and mixing the adipose particles or tissue, with the mixing element 116 in fluid and operative communication with the chambers 112, 114. Various plungers, stops, and attachment and sealing components as disclosed herein or known to one skilled in the art can be employed with the embodiment of FIG. 8 as well.

Persons skilled in the art will also recognize that other means can be used to introduce the collagenase and/or ADCS material into the target tissue without departing from the scope of the invention. For example, microneedles may be used.

Cell and adipose mixtures may be injected into the target tissue in a manner that assists in distributing and retaining the cellular mixture within the tissue for a period of time, e.g., minutes. Before, during or after injection of the cellular mixture in the corpora of the male penis, a vacuum (e.g., vacuum erection device) or other like device can be implemented to further promote the influx of blood into the penis to increase distribution and cellular viability through increased oxygenation of the tissues. Various devices, drugs and known means can be implemented to induce an erection before, during or after the injection to promote blood flow in the penis.

What is claimed is:

1. A system for treating Peyronie's disease comprising a first composition comprising collagenase, a second composition comprising adipose-derived stem cells or an apparatus capable of providing a second composition comprising adipose-derived stem cells, a cell matrix for the stem cells comprising undigested disaggregated adipose tissue, and one or more devices for delivering the first and second composition to a plaque in penile tissue, the device having a distal end with needles extendable from within a lumen of the distal end of the device so the needles are capable of piercing the plaque.

2. The system of claim 1 wherein the one or more devices for delivering the first and second composition to a plaque is a high pressure injection device capable of delivering the first composition at a pressure of at least 100 psi.

3. The system of claim 1 comprising one or more instruments for the removal of adipose tissue from a patient and the enrichment or separation of adipose-derived stem cells from the adipose tissue.

4. The system of claim 1 comprising an instrument for mixing a mechanically processed adipose tissue sample with a composition comprising a cell population enriched for adipose-derived stem cells.

5. The system of claim 1 further comprising one or more surgical instruments for obtaining an adipose tissue sample from a patient; an instrument for the enrichment or separation of adipose-derived stem cells from the adipose tissue sample; an instrument for mixing a mechanically processed adipose tissue sample with a composition comprising a cell population; and a high pressure injection device capable of delivering the composition comprising collagenase to the penile plaque at a pressure of at least 100 psi.

6. The system of claim 1 wherein the needles comprise multiple apertures.

7. The system of claim 6 wherein the apertures face outwardly from a central axis of a distal end of the device, and direct the composition outward and in a direction generally perpendicular to the central axis.

8. The system of claim 1 wherein the needles are of sizes in the range of 20 gauge to 25 gauge.

9. The system of claim 1 wherein the one or more devices for delivering the first and second composition to a plaque in penile tissue comprises a device comprising a proximal portion, a distal portion, and a shaft or body portion extending therebetween the proximal and distal portions.

10. The system of claim 9 wherein the proximal portion comprises a handle and a connection port adapted to interconnect with a fluid source, wherein the fluid source is in operative and fluid communication with the proximal portion of the device.

11. The system of claim 10 wherein the fluid source comprises a reservoir and pressure source capable of pressurizing and advancing fluid contained in the fluid source.

12. The system of claim 1 further comprising solenoid or valve configured to meter the flow of the composition from the device.

13. The system of claim 1 wherein the needles are extendable from the lumen in a non-parallel manner.

14. The system of claim 1 having two, three, four, or five needles extendable from the lumen.

15. The system of claim 1 wherein the device comprises a shaft having a lumen, and fluid delivery conduits within the lumen, wherein the needles are connected to the fluid delivery conduits which are movable within the lumen.

16. A method for treating Peyronie's disease comprising steps of: (a) delivering a composition comprising collagenase to a plaque in penile tissue, and (b) delivering a composition comprising adipose-derived stem cells to the plaque or an area of the penile tissue where the plaque existed, wherein the method uses the system of claim 1.

17. The method of claim 16, where the collagenase is delivered before the stem cells.

18. The method of claim 16, wherein collagenase in an amount of $1 \times 10^4$ to about $4 \times 10^4$ ABC units is delivered.

19. The method of claim 16, wherein the collagenase composition is delivered in a volume of 0.1 mL to about 1 mL.

20. The method of claim 16 wherein the collagenase is delivered to the plaque using an injection pressure in the range of 140 psi to 2000 psi.

21. The method of claim 16, wherein the adipose-derived stem cells are mixed with an adipose tissue derived cell matrix material to prepare the composition comprising adipose-derived stem cells.

22. A method for treating Peyronie's disease comprising steps of: (a) obtaining an adipose tissue sample from a patient with Peyronie's disease; (b) preparing an adipose stem cell composition enriched for adipose-derived stem cells from a portion of the adipose tissue sample; (c) preparing a cell injection composition comprising the substeps of mixing the adipose stem cell composition with a mechanically-processed portion of the adipose tissue; (d) delivering the composition comprising collagenase to a plaque in penile tissue using an injection pressure of at least 100 psi, and, after step (d), (e) delivering the cell injection composition to the plaque or an area of the penile tissue where the plaque existed, wherein the method uses the system of claim 1.

* * * * *